United States Patent
Yu (10) Patent No.: US 11,754,474 B2
(45) Date of Patent: Sep. 12, 2023

(54) TEST DEVICE

(71) Applicant: Quanta Vision Co., Ltd., Taipei (TW)

(72) Inventor: Ya-Chieh Yu, Taipei (TW)

(73) Assignee: QUANTA VISION CO., LTD., Taipei (TW)

( * ) Notice: Subject to any disclaimer, the term of this patent is extended or adjusted under 35 U.S.C. 154(b) by 27 days.

(21) Appl. No.: 17/530,043

(22) Filed: Nov. 18, 2021

(65) Prior Publication Data

US 2023/0152188 A1 May 18, 2023

(51) Int. Cl.
*G01N 1/14* (2006.01)
*A61B 10/00* (2006.01)

(52) U.S. Cl.
CPC ............ *G01N 1/14* (2013.01); *A61B 10/0051* (2013.01); *G01N 2001/149* (2013.01); *G01N 2001/1427* (2013.01)

(58) Field of Classification Search
CPC ............ G01N 1/14; G01N 2001/1427; G01N 2001/149; G01N 1/02; G01N 1/10; A61B 10/0051; A61B 2010/0054; A61B 10/0064; A61B 2010/0067; A61B 2010/0074
USPC .......................................... 73/864.71, 864.72
See application file for complete search history.

(56) References Cited

U.S. PATENT DOCUMENTS 4,175,439 A * 11/1979 Laker ..................... B01L 3/505
 604/11
8,474,337 B2 * 7/2013 Ohtsuka ............. A61B 10/0038
 73/864.71

FOREIGN PATENT DOCUMENTS

CN 111603203 A * 9/2020

* cited by examiner

*Primary Examiner* — Robert R Raevis
(74) *Attorney, Agent, or Firm* — Muncy, Geissler, Olds & Lowe, P.C.

(57) ABSTRACT

A test device is provided, including: a test member, including a receive portion and a first connection portion, the receive portion including a receive groove and a wall portion formed the receive groove; a moving member, inserted into the receive groove, being rotatable and movable in an axial direction to the test member, including a second connection portion; a sample collection member, formed of deformed absorption material, disposed on the moving member and disposed within the receive groove; wherein when the moving member is rotated relatively to the test member, the at least one protruding structure is moved along the at least one spiral guiding slot to move the sample collection member to rotatably axially squeeze the wall portion.

10 Claims, 7 Drawing Sheets

TEST DEVICE

BACKGROUND OF THE INVENTION

Field of the Invention

The present invention relates to a test device.

Description of the Prior Art

Conventional several inspections need inspectors and professional devices. Nowadays, the rapid test device has been widely circulated in the market for an urgent condition, so that users can test themselves with the rapid test device. The sample specimens can be saliva or other liquid for the rapid test device.

Methods of transferring fluid sample to the cassette of the conventional rapid cassette device includes a sample dropping method, a squeezing method of using a device with a volcano-shaped opening, a method of using an injection molded test device, and a method of using squeezing machine. The sample dropping method is to drop the sample into the cassette, so the sample is easy to splash. Thus, it has a high infection risk. The squeezing method of using a device with a volcano-shaped opening is perpendicularly squeezed the swab with saliva sample into the opening of the cassette. The saliva sample is easy to splash during squeezing the swab. Thus, it has a high infection risk. The method of using an injection molded test device has a saliva collection sponge and a test cassette, and the saliva collection sponge and the cassette are integrally formed of one piece. Thus, the hand of the operation is close to the saliva collection sponge during operation, so as to cause a high infection risk. In the method of using an injection molded test device, the test cassette need to be disposed within the testing machine after the test cassette has collected the saliva sample. The machine squeezing method is operated by the testing machine, so that it has disadvantages includes a large machine size, a high machine cost, and inconvenient operation.

The present invention is, therefore, arisen to obviate or at least mitigate the above-mentioned disadvantages.

SUMMARY OF THE INVENTION

The main object of the present invention is to provide a test device which prevents the sample from splashing when the sample collection member is deformed and squeezed out of the sample, so as to reduce an infection risk of the user.

To achieve the above and other objects, a test device is provided, including: a test member, including a receiving portion and a first connection portion, the receiving portion including a receiving room and a wall portion defining the receiving room; a moving member, inserted into the receiving room, being rotatable and movable in an axial direction relative to the test member, including a second connection portion, the second connection portion connected with the first connection portion, one of the first connection portion and the second connection portion including at least one spiral guiding slot, the other one of the first connection portion and the second connection portion including at least one protruding structure, the at least one protruding structure slidably engaged within the at least one spiral guiding slot; and a sample collection member, made of deformed absorbent material, connected with the moving member and disposed within the receiving room; wherein when the moving member is rotated relatively to the test member, the at least one protruding structure is moved along the at least one spiral guiding slot to move the sample collection member to rotatably axially squeeze the wall portion.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
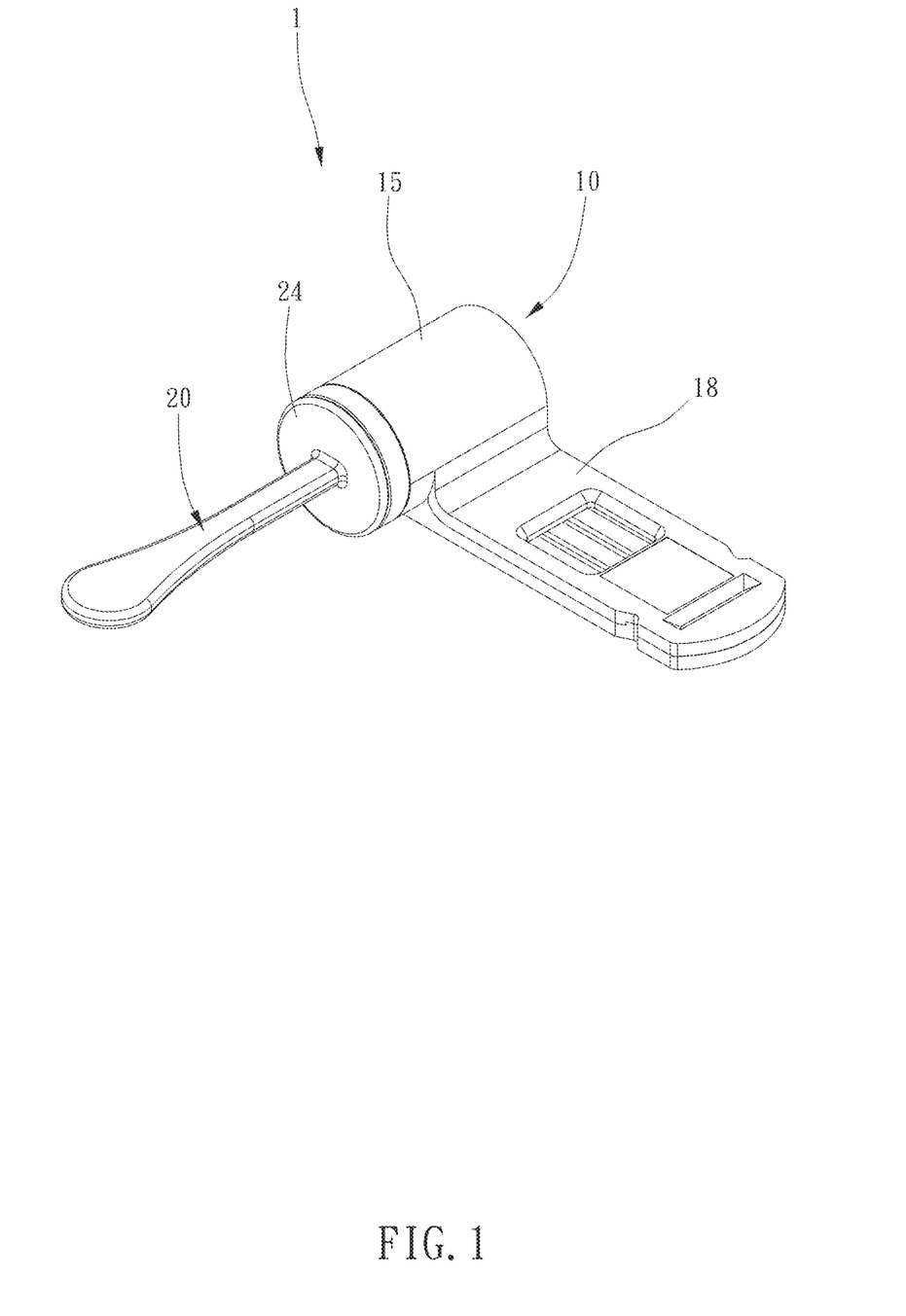
FIG. 1 is a stereogram of a preferable embodiment of the present invention.
Figure 2:
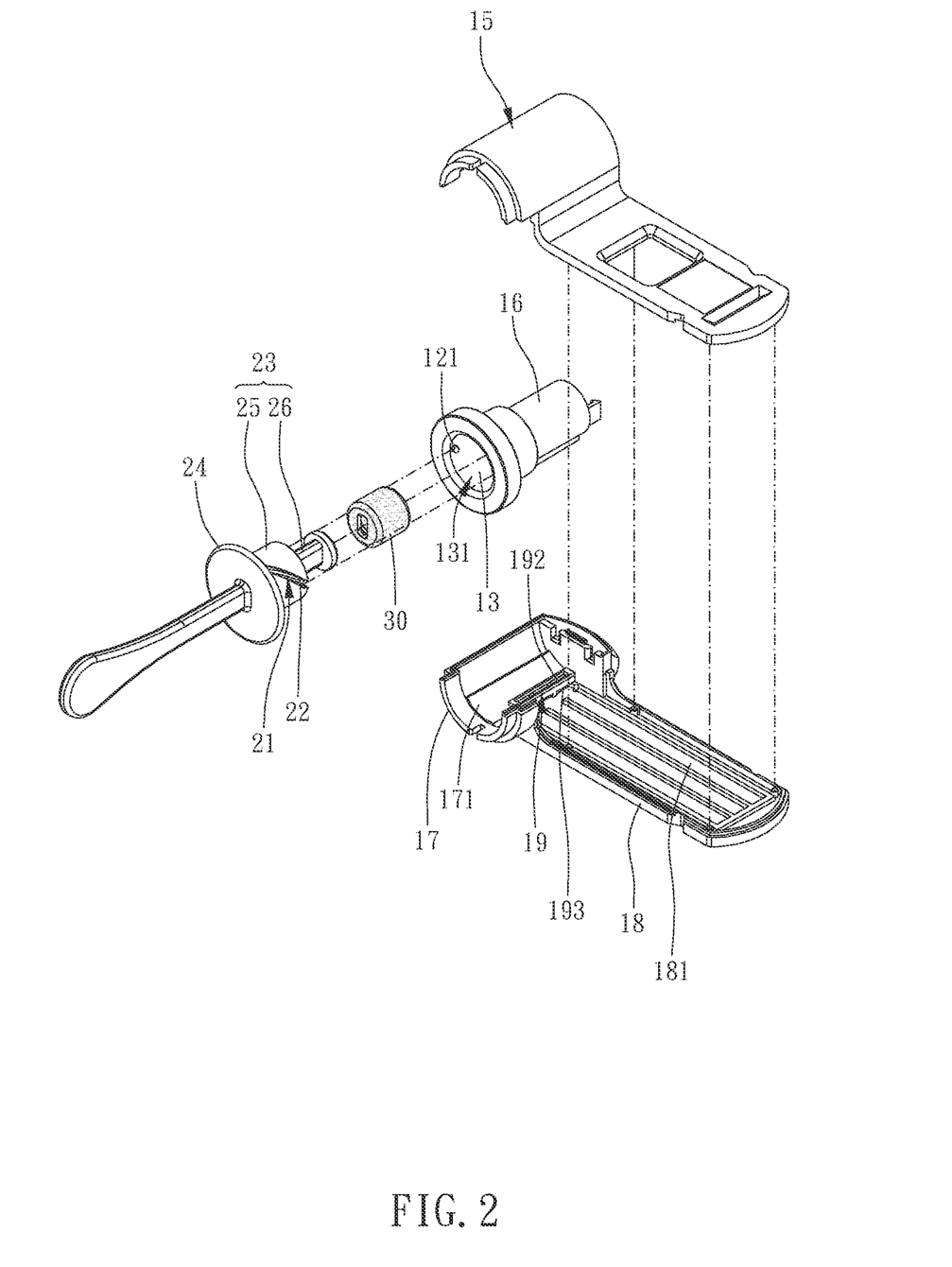
FIG. 2 is a breakdown drawing of a preferable embodiment of the present invention.
Figure 3:
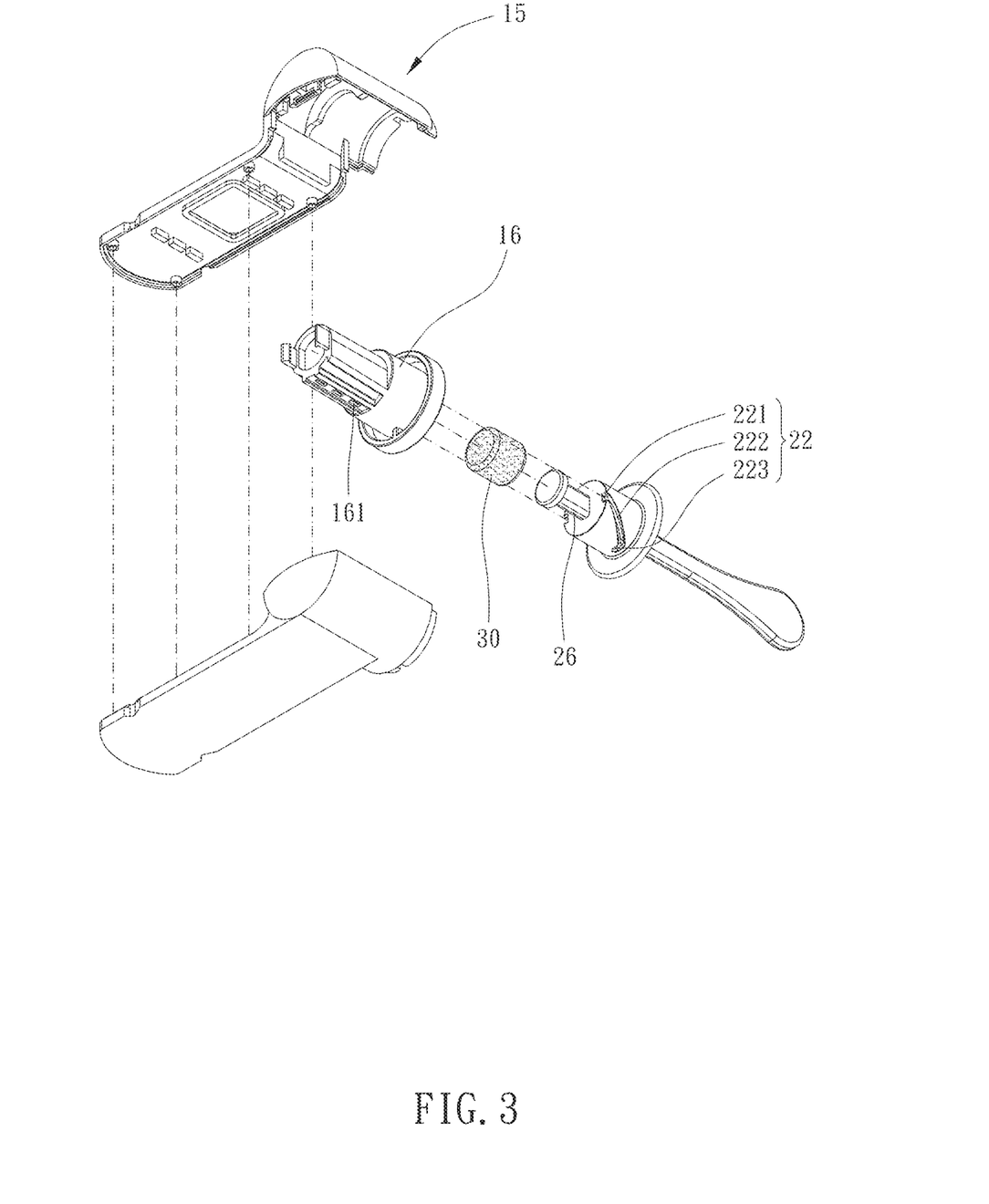
FIG. 3 is another breakdown drawing of a preferable embodiment of the present invention.
Figure 4:
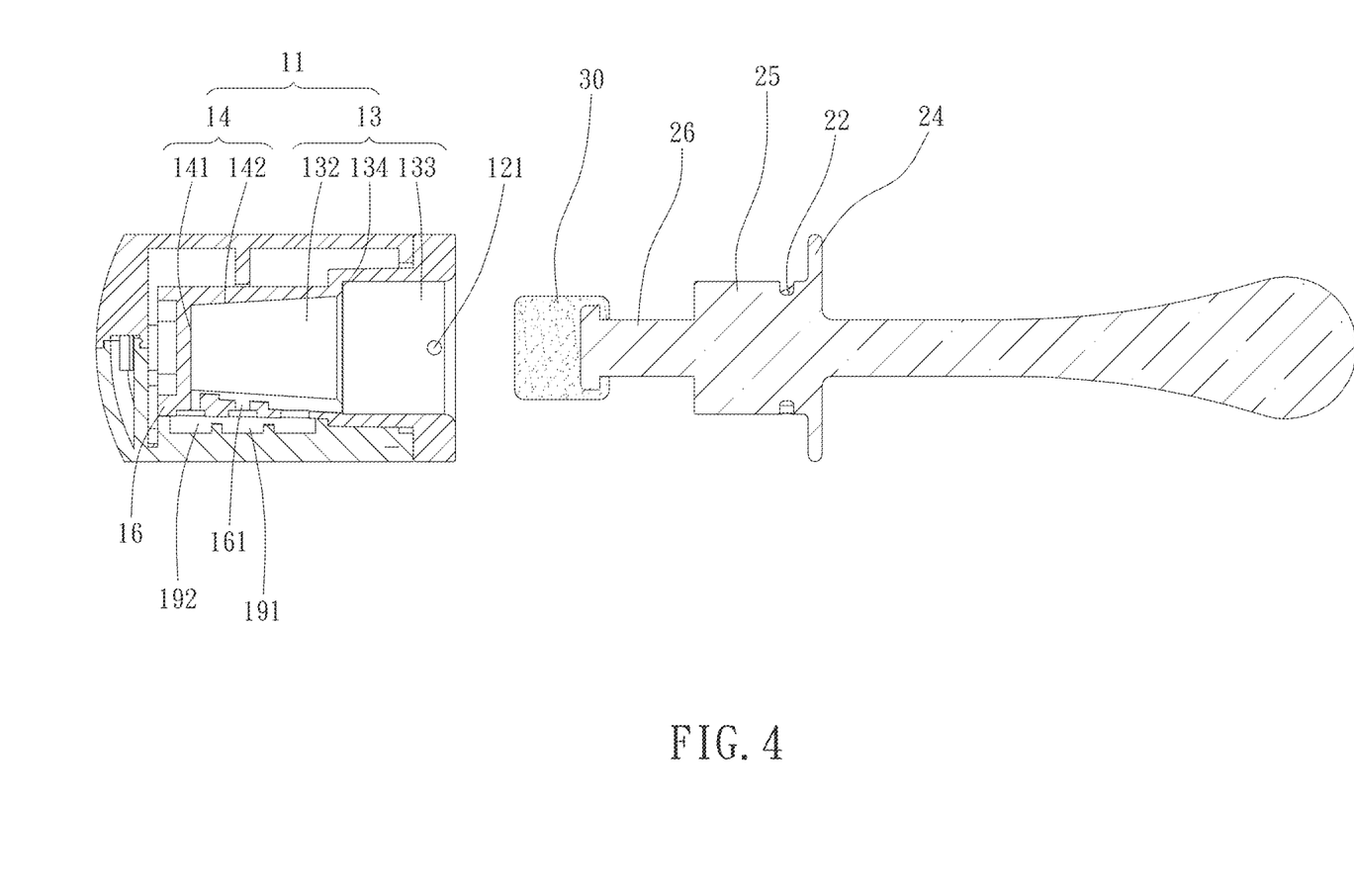
FIG. 4 is a partial cross-sectional breakdown view of a preferable embodiment of the present invention.
Figure 5:
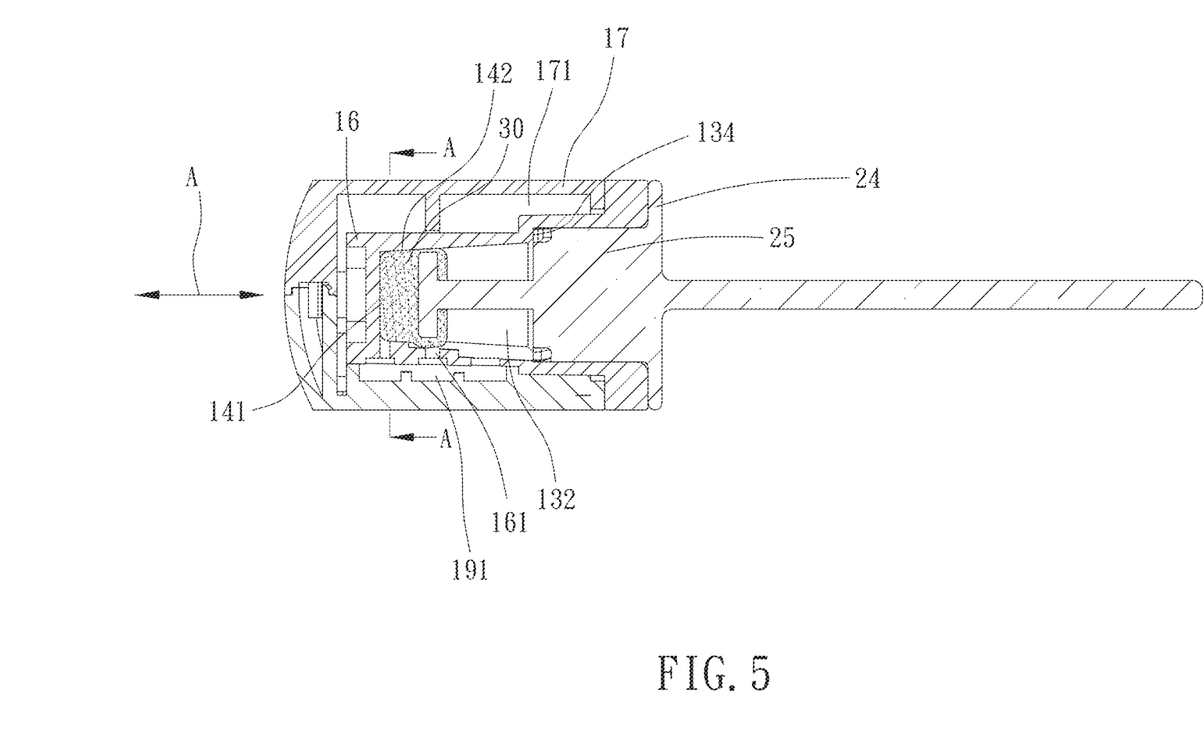
FIG. 5 is a partial cross-sectional view of a preferable embodiment of the present invention.
Figure 6:
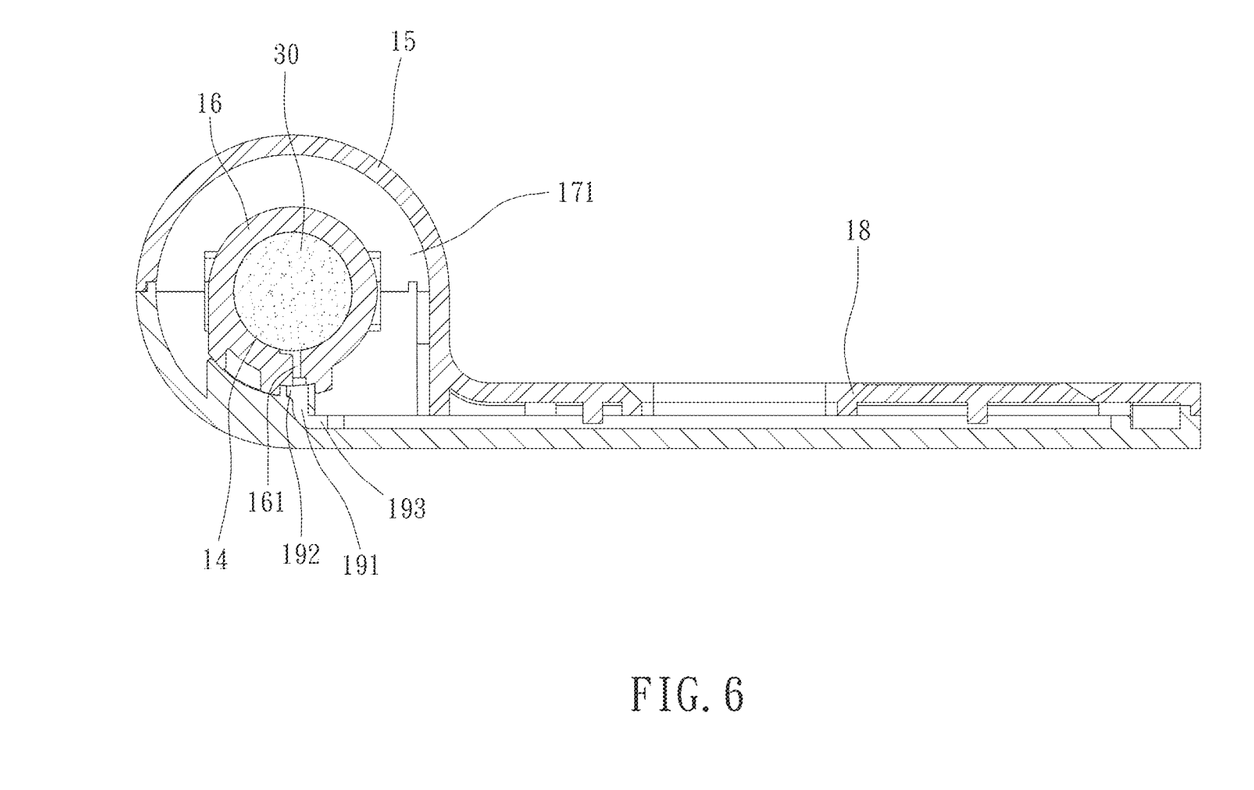
FIG. 6 is a cross-sectional view of FIG. 5, taken along a line A-A.
Figure 7:
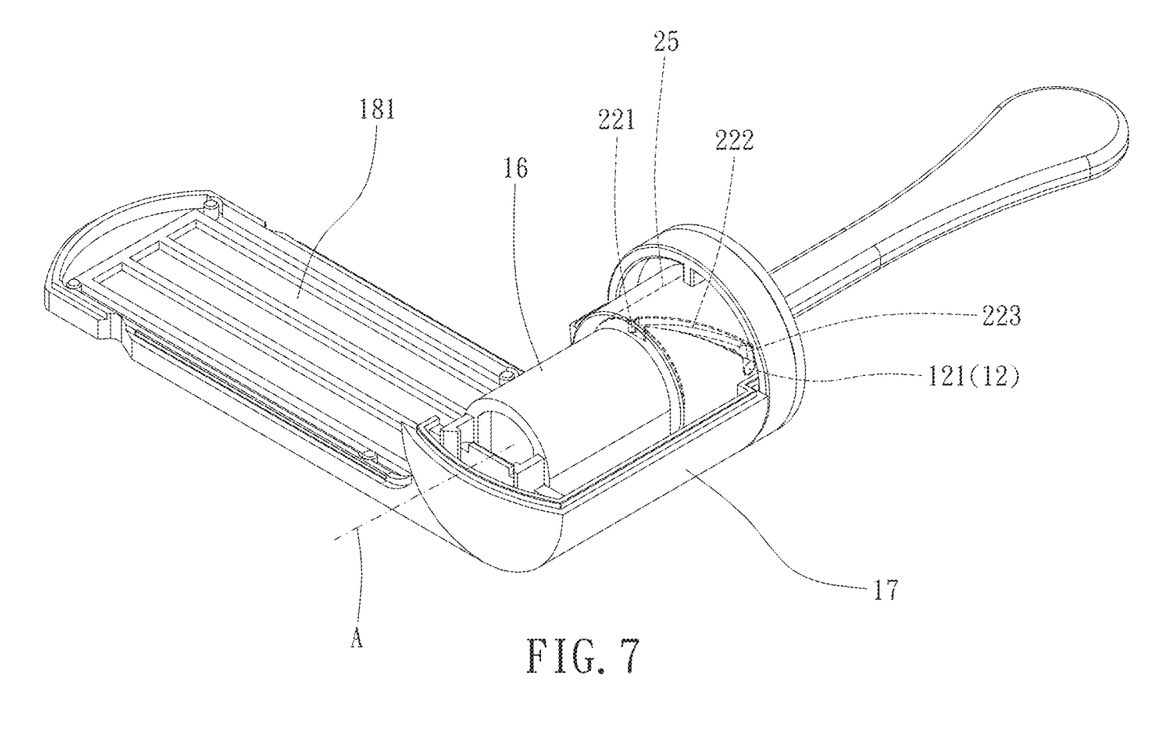
FIG. 7 is a drawing showing preferred embodiment of the present invention in use.

Please refer to FIGS. 1 to 7 for a preferable embodiment of the present invention. A test device 1 of the present invention includes a test member 10, a moving member 20 and a sample collection member 30.

The test member 10 includes a receiving portion 11 and a first connection portion 12. The receiving portion 11 includes a receiving room 13 and a wall portion 14 defining the receiving room 13. The moving member 20 is inserted into the receiving room 13, and the moving member 20 is rotatable and movable in an axial direction A relative to the test member 10. The moving member 20 includes a second connection portion 21 connected with the first connection portion 12. One of the first connection portion 12 and the second connection portion 21 includes at least one spiral guiding slot 22, and the other of the first connection portion 12 and the second connection portion 21 includes at least one protruding structure 121. The at least one protruding structure 121 is slidably engaged within the at least one spiral guiding slot 22. The spiral guiding slot 22 may be extended helically about an axis of the moving member 20 or extended obliquely in the axial direction A. The sample collection member 30 is made of deformed absorbent material, such as a sponge, a swab, and other absorbent material. The sample collection member 30 absorbs a sample, such as saliva sample and other fluid sample. The sample collection member 30 is connected with the moving member 20 and is disposed within the receiving room. Wherein when moving member 20 is rotated relatively to the test member 10, the at least one protruding structure 121 is moved along the at least one spiral guiding slot 22 to move the sample collection member 30 to rotatably axially squeeze the wall portion 14. In this embodiment, the at least one protruding structure 121 includes a plurality of protruding structures 121, and the at least one spiral guiding slot 22 includes a plurality of spiral guiding slots 22. In other embodiment, one of the protruding structure and the spiral guiding slot is a male thread, the other of the protruding structure and the spiral guiding slot is a female thread screwed to the male thread. Thus, the moving member 20 can be axially moved and rotated by a hand, so as to move the sample collection member 30 to rotatably squeeze the wall portion 14 in the axial direction A or in a radial direction and deform. Moreover, when the sample is deformed and squeezed out of the sample, it can prevent the sample from splashing, so as to reduce an infection risk of the user.

Each of the at least one spiral guiding slot 22 includes an opening end portion 221, a spiral section 222 extending helically about an axis of the moving member 20 and a restricting section 223. The opening end portion 221 is connected with an end of the spiral section 222, and the opening end portion 221 is axially opened. The restricting section 223 is transversely communicated with the spiral section 222. Each of the plurality of protruding structures 121 can be disengaged from one of the plurality of spiral guiding slot 22 by passing through the opening end portion 221 in the axial direction A. It is to be noted that, when the protruding structure 121 is engaged within the restricting section 223, the moving member 20 is positioned. Thus, the sample collection member 30 can be prevented from being pushed toward an opening 131 of the receiving room 13 when the sample collection member 30 is squeezed against the wall portion 14.

The moving member 20 includes an insertion portion 23 and a cover portion 24. The cover portion 24 is connected with the insertion portion 23. An outer diameter of the cover portion 24 is greater than an outer diameter of the insertion portion 23. The sample collection member 30 is disposed on the insertion portion 23. The insertion portion 23 is inserted within the receiving room 13, so as to prevent the sample from splashing out of the receiving room 13.

The receiving room 13 includes a tapered hole 132, the tapered hole 132 is gradually tapered in the axial direction A, the sample collection member 30 is disposed within the tapered hole 132. The receiving room 13 has the opening 131, and the wall portion 14 includes a bottom surface 141. The bottom surface 141 is disposed on a side of the receiving room 13 which is opposite to the opening 131, and the tapered hole 132 is gradually tapered toward the bottom surface 141. The sample collection member 30 abuts against the wall portion 14 and is gradually increased squeeze and deformation when the sample collection member 30 is moved toward the bottom surface 141. Thus, the sample collection member 30 can be squeezed out of a lot of sample by instantly squeezing. Preferably, the receiving room 13 further includes a wide groove 133 and a shoulder portion 134, the wide groove 133 is communicated with the tapered hole 132, the shoulder portion 134 is defined between the wide groove 133 and the tapered hole 132. The moving member 20 includes a wide section 25 and a connection section 26, and an outer diameter of the connection section 26 is less than an outer diameter of the wide section 25. The wide section 25 is connected between the cover portion 24 and the connection section 26. The outer diameter of the wide section 25 is less than an outer diameter of the cover portion 24, and the second connection portion 21 is disposed on a circumference surface of the wide section 25. The wide section 25 is inserted within the wide groove 133, the sample collection member 30 is connected with the connection section 26, the wide section 25 is blockable by the shoulder portion 134 in the axial direction A, so as to block the wide section 25 to move toward the tapered hole 132.

The test member 10 includes a test cassette 15 and a container 16. The test cassette 15 includes a collection portion 17, and a detection portion 18 and a fluid guiding portion 19. The fluid guiding portion 19 is disposed between the collection portion 17 and the detection portion 18. The collection portion 17 includes a chamber 171. The detection portion 18 includes at least one hole 181. The fluid guiding portion 19 includes at least one flow passage 191 communicated with the receiving room 131 and the at least one hole 181. Specifically, test strips or test reagent can be disposed within the at least one hole 181 to receive or absorbent the sample that is flowed from the fluid guiding portion 19, so as to provides a testing result, but not limited. The container 16 is disposed within the chamber 171, the container 16 includes the receiving portion 11 and the at least one through hole 161, and each of the at least one through hole 161 is communicated between the receiving room 13 and the at least one flow passage 191. The wall portion 14 includes a circumference wall 142, the sample collection member 30 is radially squeezed against the circumference wall 142, the circumference wall 142 extends around the axis of the moving member 20, and each of the at least one through hole 161 is disposed through the circumference wall 142 and is opened radially. The circumference wall 142 is substantially circular-shaped, so that a fluid sample squeezed from the sample collection member 30 can be guided to each through hole 161.

In this embodiment, each of the at least one flow passage 191 includes a first opening 192 and a second opening 193 which is opposite to the first opening 192. The first opening 192 is communicated with the second opening 193, the at least one through hole 161 corresponds to the first opening 192, and the hole 181 corresponds to and is communicated with the second opening 193, so that the fluid sample squeezed from the sample collection member 30 can be directly flowed into the first opening 192.

The container 16 is disassembly assembled to the test cassette 15. In this embodiment, the container 16 has at least one engagement structure which is disengageably engaged with at least one through hole of the test cassette 15, so that the container can be exchanged.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A test device, including:
   a test member, including a receiving portion and a first connection portion, the receiving portion including a receiving room and a wall portion defining the receiving room;
   a moving member, inserted into the receiving room, being rotatable and movable in an axial direction relative to the test member, including a second connection portion, connected with the first connection portion, one of the first connection portion and the second connection portion including at least one spiral guiding slot, the other one of the first connection portion and the second connection portion including at least one protruding structure, the at least one protruding structure slidably engaged within the at least one spiral guiding slot; and
   a sample collection member, made of deformed absorbent material, connected with the moving member and disposed within the receiving room;
   wherein when the moving member is rotated relatively to the test member, the at least one protruding structure is moved along the at least one spiral guiding slot to move the sample collection member to rotatably axially squeeze the wall portion.

2. The test device of claim 1, wherein each of the at least one spiral guiding slot includes an opening end portion, a spiral section extending helically about an axis of the moving member and a restricting section; the opening end portion is connected with an end of the spiral section, the opening end portion is axially opened, and the restricting section is transversely communicated with the spiral section.

3. The test device of claim 1, wherein the moving member includes an insertion portion and a cover portion; the cover portion is connected with the insertion portion, an outer diameter of the cover portion is greater than an outer diameter of the insertion portion, and the sample collection member is disposed on the insertion portion, the insertion portion is inserted within the receiving room.

4. The test device of claim 1, wherein the receiving room includes a tapered hole, the tapered hole is gradually tapered in the axial direction, and the sample collection member is disposed within the tapered hole.

5. The test device of claim 4, wherein the receiving room has an opening, the wall portion includes a bottom surface, the bottom surface is disposed on a side of the receiving room which is opposite to the opening, and the tapered hole is gradually tapered toward the bottom surface.

6. The test device of claim 1, wherein the test member includes a test cassette and a container, the test cassette includes a collection portion, a detection portion and a fluid guiding portion; the fluid guiding portion is disposed between the collection portion and the detection portion, the collection portion includes a chamber, the detection portion includes at least one hole, the fluid guiding portion includes at least one flow passage communicated with the receiving room and the at least one hole, the container is disposed within the chamber, the container includes the receiving portion and the at least one through hole, and each of the at least one through hole is communicated between the receiving room and the at least one flow passage.

7. The test device of claim 6, wherein the wall portion includes a circumference wall, the sample collection member is radially squeezed against the circumference wall, the circumference wall extends around an axis of the moving member, and each of the at least one through hole is disposed through the circumference wall and is opened radially.

8. The test device of claim 7, wherein a contour of the circumference wall is substantially circular-shaped.

9. The test device of claim 6, wherein the container is disassembly assembled to the test cassette.

10. The test device of claim 6, wherein the at least one protruding structure includes a plurality of protruding structures; the at least one spiral guiding slot includes a plurality of spiral guiding slots; each of the plurality of spiral guiding slots includes an opening end portion, a spiral section extending helically about an axis of the moving member and a restricting section; the opening end portion is connected with an end of the spiral section, the opening end portion is axially opened, the restricting section is transversely communicated with the spiral section; the moving member includes an insertion portion and a cover portion; the cover portion is connected with the insertion portion, an outer diameter of the cover portion is greater than an outer diameter of the insertion portion, the sample collection member is disposed on the insertion portion, and the insertion portion is inserted within the receiving room; the receiving room includes a tapered hole, the tapered hole is gradually tapered in the axial direction, and the sample collection member is disposed within the tapered hole; the receiving room has an opening, the wall portion includes a bottom surface, the bottom surface is disposed on a side of the receiving room which is opposite to the opening, and the tapered hole is gradually tapered toward the bottom surface; the receiving room further includes a wide groove and a shoulder portion, the wide groove is communicated with the tapered hole, the shoulder portion is defined between the wide groove and the tapered hole, the moving member includes a wide section and a connection section, an outer diameter of the connection section is less than an outer diameter of the wide section, the wide section is connected between the cover portion and the connection section, the outer diameter of the wide section is less than an outer diameter of the cover portion, the second connection portion is disposed on a circumference surface of the wide section, the wide section is inserted within the wide groove, the sample collection member is connected with the connection section, the wide section is blockable by the shoulder in the axial direction; and each of the at least one flow passage includes a first opening and a second opening which is opposite to the first opening, the first opening is communicated with the second opening, the at least one through hole corresponds to the first opening, the hole corresponds to and is communicated with the second opening.

* * * * *